(12) United States Patent
Rosier et al.

(10) Patent No.: US 7,084,293 B2
(45) Date of Patent: Aug. 1, 2006

(54) PROCESS OF SYNTHESIS OF COMPOUNDS HAVING NITRILE FUNCTIONS FROM ETHYLENICALLY UNSATURATED COMPOUNDS

(75) Inventors: Cécile Rosier, Soucieu en Jarrest (FR); Philippe Marion, Vernaison (FR); Damien Bourgeois, Lyons (FR)

(73) Assignee: Rhodia Polyamides Intermediates, Saint-Fons (FR)

(*) Notice: Subject to any disclaimer, the term of this patent is extended or adjusted under 35 U.S.C. 154(b) by 60 days.

(21) Appl. No.: 10/353,912

(22) Filed: Jan. 30, 2003

(65) Prior Publication Data

US 2004/0122251 A1 Jun. 24, 2004

(30) Foreign Application Priority Data

Dec. 23, 2002 (FR) .................................. 02 16550

(51) Int. Cl.
*C07C 253/00* (2006.01)
(52) U.S. Cl. .................. 558/335; 558/332; 556/14; 502/162
(58) Field of Classification Search .................. 558/70, 558/348, 335, 332; 556/14; 502/162
See application file for complete search history.

(56) References Cited

U.S. PATENT DOCUMENTS

| 5,512,696 A * | 4/1996 | Kreutzer et al. ............. 558/338 |
| 5,959,135 A * | 9/1999 | Garner et al. ................ 558/338 |
| 6,812,352 B1 * | 11/2004 | Kreutzer et al. ............. 549/373 |
| 6,846,945 B1 * | 1/2005 | Lenges et al. ............... 558/335 |

OTHER PUBLICATIONS

Campi et al. Aust. J. Chem, 1987,40,1053-61.*

* cited by examiner

*Primary Examiner*—Kamal A. Saeed
*Assistant Examiner*—Robert Shiao
(74) *Attorney, Agent, or Firm*—Buchanan Ingersoll, P.C.

(57) ABSTRACT

The present invention relates to a process of hydrocyanation of ethylenically unsaturated organic compounds to compounds having at least one nitrile function, particularly the hydrocyanation of diolefins such as butadiene, or of substituted olefins such as alkene nitriles such as pentenenitriles; the subject hydrocyanation is carried out in the presence of a catalytic system comprising a metallic element and mono- and pluri-dentate organophosphorus ligands.

23 Claims, No Drawings

//<br>
PROCESS OF SYNTHESIS OF COMPOUNDS HAVING NITRILE FUNCTIONS FROM ETHYLENICALLY UNSATURATED COMPOUNDS

CROSS-REFERENCE TO PRIORITY APPLICATION

This application claims priority under 35 U.S.C. § 119 of FR-02/16550, filed Dec. 23, 2002, hereby expressly incorporated by reference.

BACKGROUND OF THE INVENTION

1. Technical Field of the Invention

The present invention relates to a process of hydrocyanation of ethylenically unsaturated organic compounds to compounds having at least one nitrile function.

More particularly, it relates to the hydrocyanation of diolefins such as butadiene, or of substituted olefins such as alkene nitrites such as pentenenitriles.

2. Description of the Prior Art

French Patent No. 1,599,761 describes a process of preparation of nitrites by the addition of hydrocyanic acid to organic compounds having at least one ethylenic double bond, in the presence of a catalyst of nickel and a triaryl phosphite. This reaction can be performed with or without the presence of a solvent.

When a solvent is used in this prior art process, it is preferably a hydrocarbon such as benzene or the xylenes or a nitrile such as acetonitrile.

The catalyst used is an organic nickel complex containing ligands such as phosphines, arsines, stibines, phosphites, arsenites, or antimonites. The presence of a promoter to activate the catalyst, such as a boron compound or a metallic salt, generally a Lewis acid, is likewise already recommended in the said patent.

Much work has been carried out to find catalytic systems generally comprising an organophosphorus ligand and a catalytically active metal, more particularly nickel, and exhibiting higher and higher performances.

The performance of a catalytic system is evaluated by determining several characteristics such as, in particular, the stability of the catalytic activity of the system, the yield of the reaction, and the selectivity in the synthesis of advantageous products: in the present case, the selectivity for linear pentenenitriles or for adiponitrile.

Thus it was proposed at an earlier time to use as a catalytic system, nickel associated with organophosphorus ligands possessing a single phosphorus atom, termed monodentate ligands. The industrially used compound of this class of products is tritolyl phosphite (TTP). This system has very acceptable performance in the synthesis of pentenenitriles by the hydrocyanation of butadiene, but a performance in need of improvement for the synthesis of adiponitrile by hydrocyanation of pentenenitriles.

Furthermore, this catalytic system has good stability and solubility in the reaction medium. Such catalytic systems have been described in numerous patents such as, for example, U.S. Pat. No. 3,496,215, DE 19953058, FR 1,529, 134, FR 2,069,411, U.S. Pat. Nos. 3,631,191 and 3,766,231, FR 2,523,974.

To obtain catalytic performance, in particular high selectivity in the step of hydrocyanation of alkene nitriles, more particularly pentenenitriles, to dinitriles, a new class of organophosphorus ligands has been proposed, specifically intended to be associated with nickel. This new class of ligands comprises organophosphorus compounds possessing several phosphorus atoms, termed pluridentate ligands. Among these, the proposed compounds are generally compounds including two phosphorus atoms, termed bidentate ligands.

Such compounds and catalytic systems are protected by numerous patents. By way of example, there can be mentioned WO 99/06355, WO 99/06356, WO 99/06357, WO 99/06358, WO 99/52632, WO 99/65506, WO 99/62855, U.S. Pat. No. 5,693,843, WO 96/1182, WO 96/22968, U.S. Pat. No. 5,981,772, WO 01/36429, WO 99/64155, and WO 02/13964.

The structure of these compounds is more or less complex, particularly as regards the groups carried by the phosphorus atoms and the structure connecting together the two phosphorus atoms.

With this class of bidentate ligands, it is possible to obtain a catalytic system having in particular a better selectivity in the production of linear dinitriles in the process of hydrocyanation of an alkene nitrile.

However, these bidentate ligands of more complex structure are more difficult to synthesize, making their cost higher. Consequently, it is necessary and important that their stability in the reaction medium is very high to permit utilization in an industrial process from an economic viewpoint. Furthermore, taking account of their complex structure, their solubility in the reaction medium can be reduced and can lead to a lowering of catalytic activity and thus of the total yield of the hydrocyanation reaction.

SUMMARY OF THE INVENTION

One of the objects of the present invention is to propose a solution which permits catalytic systems based on pluridentate ligands to be used, specifically having the characteristics of elevated selectivity, while reducing the disadvantages linked to their instability and their level of solubility.

For this purpose, the invention proposes a process of hydrocyanation of compounds comprising at least one ethylenic unsaturation by reaction with hydrogen cyanide, in the presence of a catalytic system comprising a metallic element having catalytic activity associated with organophosphorus ligands chosen from the group comprising organophosphonites, organophosphinites, organophosphines, organophosphites, and organophosphoramides, characterized in that the catalytic system comprises at least two organophosphorus ligands, a first ligand being chosen from the group of monodentate organophosphite compounds, and a second ligand chosen from the group of pluridentate organophosphorus ligands.

DETAILED DESCRIPTION OF BEST MODE AND SPECIFIC/PREFERRED EMBODIMENTS OF THE INVENTION

According to a preferred characteristic of the invention, the ratio of number of moles of the second ligand expressed in phosphorus atoms to the number of atoms of the metallic element is at least equal to 1, and is preferably comprised between 1 and 6, advantageously comprised between 1 and 5 and more preferably comprised between 1 and 4.

According to another characteristic of the invention, the ratio of the total number of moles of organophosphorus ligands expressed in number of phosphorus atoms to the number of atoms of metallic element is comprised between 2 and 100. However, this ratio is not critical. "Total number of moles of organophosphorus ligands" is to be understood to mean the sum of moles of the first and second ligands According to yet another preferred characteristic of the invention, the ratio of the number of moles of the first ligand and the number of moles of the second ligand is advantageously greater than 0.1, and more advantageously, greater than or equal to 0.5.

The organophosphorus ligands suitable as the first ligand are chosen from the group comprising monodentate organophosphite compounds such as the compounds of the following general formula (I)

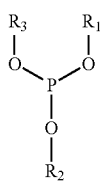

in which $R_1$, $R_2$, and $R_3$, identical or different, represent a linear or branched alkyl radical having 1–12 carbon atoms and possibly including heteroatoms, an aromatic or cycloaliphatic radical, substituted or unsubstituted, which can include heteroatoms, and one or more rings of condensed form or not, with the radicals $R_1$, $R_2$, $R_3$, able to be connected together two by two.

As an example of monodentate organophosphite compounds suitable for the invention, there can be mentioned triphenylphosphite, tritolylphosphite, and trithymol phosphite.

Tritolylphosphite is the preferred compound, because it has good solubility in the reaction medium and is relatively inexpensive.

The organophosphorus compounds which are suitable for the second ligand are in particular the bidentate organophosphorated compounds of the following general formula II:

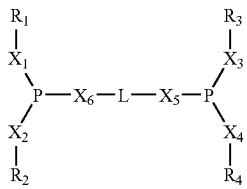

in which $R_1$, $R_2$, $R_3$, and $R_4$, identical or different, represent a linear or branched alkyl radical having 1–12 carbon atoms, which can include heteroatoms; an aromatic or cycloaliphatic radical, substituted or unsubstituted, which can include heteroatoms and one or more rings in condensed form or not; an alkylaryl radical; or an arylalkyl radical; where the radicals $R_1$ and $R_2$, and/or $R_3$ and $R_4$, can be connected together, $X_1$, $X_2$, $X_3$, $X_4$, $X_5$, and $X_6$, identical or different, represent a covalent bond, an oxygen atom, or a divalent —$NR_5$— radical in which $R_5$ represents a hydrogen atom or an alkyl, aryl, sulfonyl, cycloalkyl, or carbonylated radical, and L represents a covalent bond or a divalent linear alkyl radical having 1–12 carbon atoms, which can include heteroatoms; a divalent cycloaliphatic or aromatic radical, which can include heteroatoms, substituted or unsubstituted, able to include several rings in condensed form or not; a divalent alkylaryl or arylalkyl radical.

As examples of bidentate organophosphorus compounds, there can be cited the compounds described in the patents or patent applications cited hereinabove.

Likewise, there can be more particularly mentioned as second ligands the compounds exemplified in the following patents: WO 95/30680, WO 96/11182, WO 99/06358, WO 99/13983, WO 99/64155, WO 01/21579, and WO 01/21580.

The following structures are given by way of example, wherein Ph means phenyl.

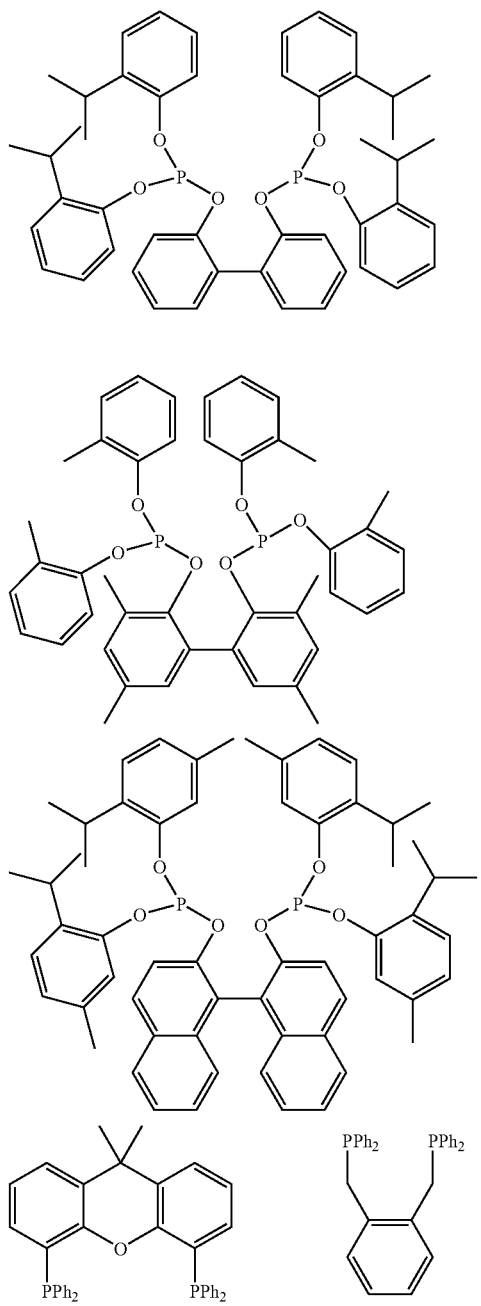

-continued

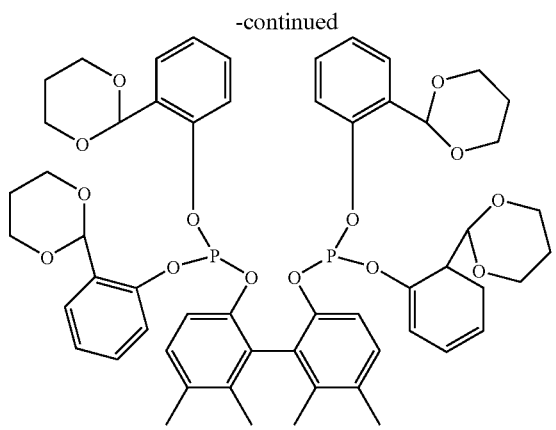

These compounds have a more complex structure than the first ligands described hereinabove and often have poor solubility in the reaction medium and greater instability. However, these second ligands, or bidentate ligands, have better catalytic properties, particularly as regards selectivity for nitriles or dinitriles.

According to the process of the invention, the use of a mixture of two ligands, monodentate and pluri (bi)dentate, enables the catalytic properties of the pluri (bi)dentate compound to be preserved, particularly as regards selectivity, while improving their stability in the reaction medium.

According to the invention, the catalytic system can be defined symbolically by the following general formula III:

$$M[L_1]_x[L_2]_y \qquad (III)$$

in which M represents a transition metal having catalytic activity; $L_1$ represents the monodentate organophosphorus first ligand; $L_2$ represents the pluridentate organophosphorus second ligand; x and y represent a decimal number corresponding to the number of moles of the respective ligand in the catalytic system.

According to a preferred characteristic of the invention, the metallic element M having catalytic activity is chosen from the group comprising nickel, cobalt, iron, ruthenium, rhodium, palladium, osmium, iridium, platinum, copper, silver, gold, zinc, cadmium and cerium.

This formula is given solely by way of indication and does not mean that each metal atom M is coordinated with the two ligands. Thus it is possible that a portion of the metal atoms M is coordinated solely with the first ligand, the other portion of the atoms with the second ligand, and finally, a last portion with the two ligands in variable proportions. The above formula has only been given as an indication and for clarity, and is based on the quantities of compounds used and not on a structural analysis of the catalytic system obtained.

The preparation of the organometallic complexes forming the above metallic system can be performed by placing in contact a solution of a compound of a chosen metal with a solution of each ligand (first or second) or a solution of these two ligands.

The metal compound can be dissolved in a solvent.

The metal can be present in the compound used either at the degree of oxidation which it will have in the organometallic complex, or at a higher degree of oxidation.

For example, it can be indicated that in the organometallic complexes of the invention, rhodium is at the degree of oxidation (I), ruthenium at the degree of oxidation (II), platinum at the degree of oxidation (0), palladium at the degree of oxidation (0), osmium at the degree of oxidation (II), iridium at the degree of oxidation (I), nickel at the degree of oxidation (0).

If the metal is used at a higher degree of oxidation during the preparation of the organometallic complex, it can be reduced in situ.

Compounds of transition metals, more particularly compounds of nickel, palladium, iron, or copper, are preferably utilized as the transition metal.

Among the compounds mentioned hereinabove, the most preferable compounds are those of nickel.

As non-limitative examples, there can be mentioned:
compounds in which nickel has degree of oxidation zero, such as potassium tetracyano nickelate, $K_4[Ni(CN)_4]$; bis(acrylonitrile) nickel zero; bis(1,5-cyclooctadiene nickel (likewise termed $Ni(cod)_2$), and derivatives containing ligands such as tetrakis (triphenylphosphine) nickel zero.

nickel compounds such as carboxylates (particularly acetate), carbonate, bicarbonate, borate, bromide, chloride, citrate, thiocyanate, cyanide, formate, hydroxide, hydrophosphite, phosphite, phosphate and derivatives, iodide, nitrate, sulfate, sulfite, aryl and alkyl sulfonates.

When the nickel compound used corresponds to a state of oxidation of nickel greater than zero, a nickel reducing agent is added to the reaction medium and preferentially reacts with nickel under the reaction conditions. This reducing agent can be organic or inorganic. As non-limitative examples, there may be mentioned borohydrides such as $NaBH_4$, $KBH_4$, Zn powder, magnesium, or hydrogen.

When the nickel compound used corresponds to the 0 oxidation state of nickel, a reducing agent of the abovementioned type can likewise be added, but this addition is not imperative.

When an iron compound is used, the same reducing agents are suitable.

In the case of palladium, the reducing agents can in addition be elements of the reaction medium (organophosphorated compound, solvent, olefin).

The solutions of the first and second ligands can be added simultaneously or successively. Furthermore, it is possible to prepare the organometallic complexes with each ligand separately, then to mix the two systems before introducing them into the reaction medium, or to introduce them directly into the said medium.

The organic compounds having at least one ethylenic double bond more particularly used in the present process are diolefins such as butadiene, isoprene, 1,5-hexadiene, 1,5-cyclooctadiene, ethylenically unsaturated aliphatic nitriles, particularly the linear pentenenitriles such as 3-pentenenitrile, 4-pentenenitrile; monoolefins such as styrene, methylstyrene, vinyl naphthalene, cyclohexene, methyl cyclohexene, and also mixtures of several of these compounds. The pentenenitriles can particularly contain amounts, generally minor, of other compounds, such as 2-methyl-3-butenenitrile, 2-methyl-2-butenenitrile, 2-pentenenitrile, valeronitrile, adiponitrile, 2-methylglutaronitrile, 2-ethylsuccinonitrile, or butadiene, arising for example from the prior hydrocyanation reaction of butadiene to unsaturated nitriles.

Indeed, during the hydrocyanation of butadiene, nonnegligible amounts of 2-methyl-3-butenenitrile and 2-methyl-2-butenenitrile are formed with the linear pentenenitriles. The catalytic system used for the hydrocyanation according to the process of the invention can be prepared before its introduction into the reaction zone, for example, by the addition, to mixtures of the first and second ligands alone or dissolved in a solvent, of the appropriate quantity of the chosen transition metal compounds and possibly of the reducing agent, or according to the process described hereinabove. It is likewise possible to prepare the catalytic system "in situ" by the simple addition of the first and second ligands and of the transition metal compound to the hydrocyanation reaction medium, before or after the addition of the compound to undergo hydrocyanation.

The quantity of a nickel or other transition metal compound used is chosen to obtain a concentration, in moles of transition metal per mole of organic compounds to undergo hydrocyanation or isomerization, between $10^{-4}$ and 1, preferably between 0.0003 and 0.5 mole per mole of nickel or other transition metal used.

The total quantity of organophosphorus ligands used to form the catalyst is chosen such that the number of moles of these compounds with respect to one mole of transition metal is 0.5–500 and preferably 2–100.

Although the reaction is generally conducted without solvent, it can be advantageous to add an inert organic solvent. The solvent can be a solvent of the catalyst which is miscible at the hydrocyanation temperature with the phase including the compound to undergo hydrocyanation. As examples of such solvents, there can be mentioned aromatic, aliphatic, or cycloaliphatic hydrocarbons.

The hydrocyanation reaction is generally performed at temperature of 10° C. to 200° C. and preferably from 30° C. to 120° C. It can be performed in a medium possessing one phase or two phases.

The process of the invention can be carried out continuously or discontinuously.

The hydrogen cyanide used can be prepared from metallic cyanides, particularly sodium cyanide, or from cyanhydrins, such as acetone cyanhydrin, or by any other known process of synthesis.

The hydrogen cyanide is introduced into the reactor in gaseous or liquid form. It can also be dissolved beforehand in an organic solvent.

In the context of discontinuous performance, there can be charged into a reactor, purged beforehand with an inert gas (such as nitrogen, argon) either a solution containing the whole or a portion of the various constituents, such as the compound to undergo hydrocyanation, the compounds of formulas (I) and (II), the transition metal compound, the possible reducing agent and solvent; or the said constituents separately. The reactor is generally then brought to the chosen temperature. The hydrogen cyanide is then introduced, preferably in a continuous and regular manner.

When the reaction (the progress of which can be followed by assay of samples) has finished, the reaction mixture is withdrawn after cooling, and the reaction products are isolated, for example by distillation.

The process of hydrocyanation of ethylenically unsaturated compounds according to the present invention likewise relates to the hydrocyanation of the said ethylenically unsaturated nitriles obtained hereinabove by reaction with hydrogen cyanide, and consists of utilizing a catalytic system conforming to the present invention with a co-catalyst consisting of at least one Lewis acid.

The ethylenically unsaturated compounds which can be used in this step are generally those cited for the basic process. However, it is more particularly advantageous to apply it to the reaction of hydrocyanation to dinitriles of ethylenically unsaturated aliphatic nitriles, particularly to linear pentenenitriles such as 3-pentenenitrile, 4-pentenenitrile, and their mixtures.

These pentenenitriles can contain generally minor quantities of other compounds, such as 2-methyl-3-butenenitrile, 2-methyl-2-butenenitrile, 2-pentenenitrile, valeronitrile, adiponitrile, 2-methyl glutaronitrile, 2-ethyl succinonitrile, or butadiene, arising from the previous hydrocyanation reaction of butadiene and/or from the isomerization of 2-methyl-3-butenenitrile to pentenenitriles.

In the case of hydrocyanation of ethylenically unsaturated aliphatic nitrites, the Lewis acid used as co-catalyst particularly enables the linearity of the obtained dinitriles to be improved, that is, the percentage of linear dinitrile with respect to the total dinitriles formed, and/or the activity and lifetime of the catalyst to be increased.

By "Lewis acid" in the present text is intended the usual definition, namely, compounds which are electron pair acceptors.

In particular, the Lewis acids mentioned in the volume edited by G. A. Olah, "Friedel-Crafts and Related Reactions," Vol. 1, pages 191–197 (1963) can be used.

The Lewis acids which can be used as co-catalysts in the present process are chosen from among the compounds of elements of Groups Ib, IIb, IIIa, IIIb, IVa, IVb, Va, Vb, VIb, VIIb and VIII of the Periodic Table of the elements. These compounds are most often salts, particularly halides, such as chlorides or bromides; sulfates, halogenoalkyl sulfonates, or perhalogenoalkyl sulfonates, particularly fluoroalkyl sulfonates or perfluoroalkyl sulfonates, halogenoacetates, perhalogenoacetates, carboxylates, and phosphates.

As non-limitative examples of such Lewis acids, there can be mentioned zinc chloride, zinc bromide, zinc iodide, manganese chloride, manganese bromide, cadmium chloride, cadmium bromide, stannous chloride, stannous bromide, stannous sulfate, stannous tartrate, indium chloride, indium trifluoromethylsulfonate, indium trifluoroacetate, the chlorides or bromides of rare earth elements such as lanthanum, cerium, praseodymium, neodymium, samarium, europium, gadolinium, terbium, dysprosium, hafnium, erbium, thallium, ytterbium and lutetium, cobalt chloride, ferrous chloride, and yttrium chloride.

Compounds such as triphenylborane and titanium isopropylate can also be used as Lewis acids.

Mixtures of several Lewis acids can of course be used.

Among the Lewis acids there are more particularly preferred zinc chloride, zinc bromide, stannous chloride, stannous bromide, triphenylborane, indium trifluoromethylsulfonate, and zinc chloride/stannous chloride mixtures.

The Lewis acid co-catalyst used generally represents 0.01–50 moles per mole of transition metal compound, more particularly of nickel compound.

As in performing the basic process of the invention, the catalytic system used for hydrocyanation in the presence of a Lewis acid can be prepared before its introduction into the reaction zone, or in situ, for example by addition to the reaction zone of the different components of the catalytic system.

It is likewise possible, under the conditions of the hydrocyanation process of the present invention, and particularly operating in the presence of the previously described catalytic system comprising at least one monodentate ligand and a bidentate ligand and at least one transition metal compound, to perform, in the absence of hydrogen cyanide, the isomerization of 2-methyl-3-butenenitrile into pentenenitriles, and more generally, branched unsaturated nitrites into linear unsaturated nitrites.

The 2-methyl-3-butenenitrile subjected to isomerization according to the invention can be used alone or in a mixture with other compounds.

Thus 2-methyl-3-butenenitrile can be used in a mixture with 2-methyl-2-butenenitrile, 4-pentenenitrile, 3-pentenenitrile, 2-pentenenitrile, butadiene, adiponitrile, 2-methyl glutaronitrile, 2-ethyl succinonitrile, or valeronitrile.

It is of particular interest to treat the reaction mixture from the hydrocyanation of butadiene with HCN in the presence of at least one mixture of compounds of formulae (I) and (II) and at least one transition metal compound, more preferably a nickel compound of degree of oxidation 0, as previously defined.

In the context of this preferred alternative, the catalytic system being already present for the hydrocyanation reaction of butadiene, it is sufficient to stop any introduction of hydrogen cyanide, to allow the isomerization reaction to proceed.

If need be, a slight flushing of the reactor with an inert gas such as nitrogen or argon can be performed in order to expel the hydrogen cyanide which could still be present.

The isomerization reaction is generally performed at a temperature of 10° C. to 200° C., and preferably from 60° C. to 180° C.

In the preferred case of isomerization immediately following the hydrocyanation reaction of butadiene, it will be advantageous to operate at the temperature at which the hydrocyanation was carried out.

As in the case of hydrocyanation of ethylenically unsaturated compounds, the catalytic system used for the isomerization can either be already present in the medium or prepared according to the fashion already described hereinabove.

Although the isomerization reaction is generally performed without solvent, it can be advantageous to add an inert organic solvent, which could be the solvent for the later extraction. This is particularly the case when such a solvent has been used in the butadiene hydrocyanation reaction, and serves to prepare the medium subjected to the isomerization reaction. Such solvents may be chosen from among those which have been mentioned hereinabove for hydrocyanation.

However, the preparation of dinitrile compounds by hydrocyanation of an olefin such as butadiene can be performed by using a catalytic system conforming to the invention for the above steps of formation of unsaturated nitrites and of isomerization; the hydrocyanation reaction of the unsaturated nitrites to dinitriles can be performed with a catalytic system according to the invention or any other catalytic system already known for this reaction.

Similarly, the olefin hydrocyanation reaction to unsaturated nitrites and the isomerization of the latter can be performed with a different catalytic system than that of the invention, the step of hydrocyanation of unsaturated nitrites to dinitriles being performed with a catalytic system according to the invention.

The following examples illustrate the invention.

In the examples, the abbreviations used have the meanings indicated below.

cod: 1,5-cyclooctadiene
eq: equivalent
3PN: 3-pentenenitrile
4PN: 4-pentenenitrile
3+4PN: 3PN+4PN
TT(Y): Transformation ratio of product Y to undergo hydrocyanation, corresponding to the ratio of the number of moles of Y transformed to the initial number of moles of Y.
Linearity (L): Ratio of the number of moles of adiponitrile (AdN) formed to the number of moles of dinitriles formed (sum of moles of adiponitrile (AdN), ethylsuccinyl dinitrile (ESN), and methylglutaronitrile (MGN)).
Selectivity (%): Number of moles of AdN formed with respect to the theoretical number of moles of AdN, calculated from the number of moles of 3+4pn transformed.
CPG: gas phase chromatography
ml: milliliter
mol: mole
mmol: millimole
Ph: phenyl

EXAMPLES 1–12

These trials relate to the hydrocyanation of pentenenitriles to adiponitrile. These trials were performed according to four operating modes described hereinafter.

Operating Mode 1:

Under an inert atmosphere, there are charged successively into a 60-ml Schott glass tube equipped with a septum stopper:
  the ligand (6 mole eq of ligand/Ni for monodentate ligands, 3 moles eq of ligand/Ni for bidentate ligands);
  3-pentenenitrile (1.25 g, 400 eq/Ni);
  bis(1,5-cyclooctadiene)$_2$ nickel (21 mg);
  the Lewis acid (1 eq/Ni).

The reaction medium is heated to 70° C., with agitation. Acetone cyanhydrin is fed into the medium by a pressure syringe with a throughput of 0.45 ml per hour. After 3 hours of injection, the introduction of acetone cyanhydrin is stopped. The mixture is cooled to ambient temperature, diluted with acetone, and analyzed by gas phase chromatography.

Operating Mode 2:

Under an inert atmosphere, there are charged successively into a 60-ml Schott glass tube equipped with a septum stopper:
  the bidentate ligand (1 mole eq of ligand/Ni);
  the bidentate ligand (4 mole eq of ligand/Ni);
  3-pentenenitrile (1.25 g, 400 eq/Ni);
  bis(1,5-cyclooctadiene)$_2$ nickel (21 mg);
  the Lewis acid (1 eq/Ni).

The reaction medium is then heated to 70° C. under agitation. Acetone cyanhydrin is fed into the medium by a pressure syringe with a throughput of 0.45 ml per hour. After 3 hours of injection, the introduction of acetone cyanhydrin is stopped. The mixture is cooled to ambient temperature, diluted with acetone, and analyzed by gas phase chromatography.

Operating Mode 3:

Under an inert atmosphere, there are successively charged into a 100 ml stainless steel reactor:
  the ligand (6 mole eq of ligand/Ni for monodentate ligands; 3 eq mole of ligand/Ni for bidentate ligands);
  3-pentenenitrile (30 g, 75 eq/Ni);
  bis(1,5-cyclooctadiene)$_2$ nickel (1.30 g);
  the Lewis acid (1 eq/Ni).

The reaction medium is then heated under agitation at 55° C. Liquid HCN is added to the reaction medium by a pressure syringe with a throughput of 1.92 ml per hour. After 5 hours of injection, the introduction of HCN is stopped. The mixture is cooled to ambient temperature, diluted with acetone, and analyzed by gas phase chromatography.

Operating Mode 4:

Under an inert atmosphere, there are successively charged into a 100 ml stainless steel reactor:

the bidentate ligand (1 mole eq of ligand/Ni);
the monodentate ligand (4 mole eq of ligand/Ni);
3-pentenenitrile (30 g, 75 eq/Ni);
bis(1,5-cyclooctadiene)$_2$ nickel (1.30 g);
the Lewis acid (1 eq/Ni).

The reaction medium is then heated under agitation at 55° C. Liquid HCN is added to the reaction medium by a pressure syringe with a throughput of 1.92 ml per hour. After 5 hours of injection, the introduction of HCN is stopped. The mixture is cooled to ambient temperature, diluted with acetone, and analyzed by gas phase chromatography.

The results obtained are collected in Table 1 below:

TABLE 1

| Ex. | Ligand Used | Ratio L/Ni | Lewis Acid | Operating Mode | L(%) | Selectivity AdN(%) | Solubility |
|---|---|---|---|---|---|---|---|
| 1 | Ligand C | 6 | ZnCl$_2$ | 1 | 86 | 79 | Yes |
| 2 | Ligand C | 2 | ZnCl$_2$ | 1 | 83 | 73 | Yes |
| 3 | Ligand A | 6 | ZnCl$_2$ | 1 | 76 | 61 | Yes |
| 4 | Ligand C + A | 2–4 | ZnCl$_2$ | 1' | 84 | 82 | Yes |
| 5 | Ligand C | 6 | ZnCl$_2$ | 1 | 86 | 79 | Yes |
| 6 | Ligand C | 2 | ZnCl$_2$ | 1 | 83 | 73 | Yes |
| 7 | Ligand B | 6 | ZnCl$_2$ | 1 | 54 | 13 | Yes |
| 8 | Ligand C + B | 2–4 | ZnCl$_2$ | 1' | 83 | 74 | Yes |
| 9 | Ligand D | 6 | InTFA$_3$ | 2 | 92 | 81 | No |
| 10 | Ligand D | 2 | InTFA$_3$ | 2 | 74 | (1) | Yes |
| 11 | Ligand A | 6 | InTFA$_3$ | 2 | 81 | 75 | Yes |
| 12 | Ligand D + A | 2–4 | InTFA$_3$ | 2' | 92 | 81 | Yes |

(1) The selectivity could not be determined because the rate of transformation was too low.
InTFA$_3$: indium trifluoroacetate.

The L/Ni ratio is expressed in phosphorus atoms per nickel atom; the first ratio relates to the ratio of phosphorus atoms provided by the first ligand, and the second ratio relates to the phosphorus atoms provided by the first ligand.

ligand A: tritolyl phosphite.
ligand B: trithymol phosphite.

Ligand C:

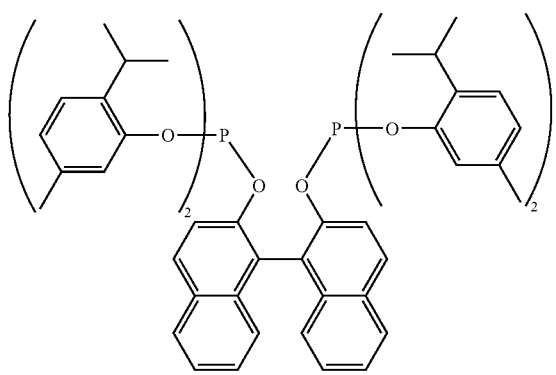

Ligand D:

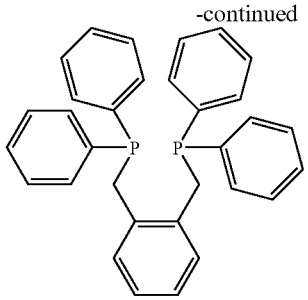

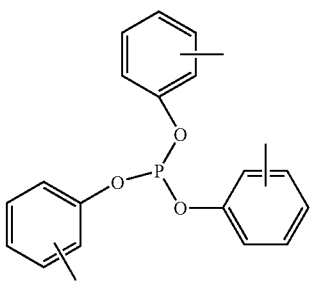

EXAMPLE 13

Hydrolysis of a mixture of ligands of the following formulas:

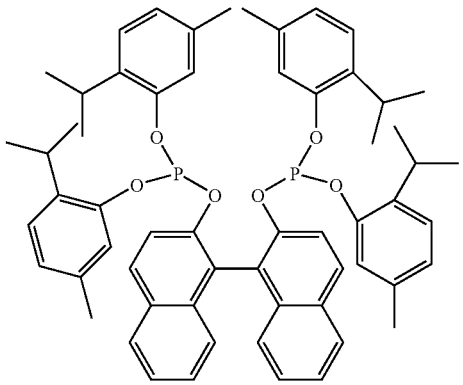

In a glove box, there are successively introduced into a 30 ml Schott type tube: ligand C (270 mg), ligand A (2 eq.), 3-pentenenitrile (1.0 g), and zinc chloride (2 eq). A clear, homogeneous mixture is obtained, which is agitated under an inert atmosphere and to which 2 eq of water are added. The composition of the mixture is then analyzed by $^{31}$P NMR.

The following results are obtained:

TABLE 2

| Time | Proportion of C, by Weight | Proportion of A, by weight |
|---|---|---|
| 15 minutes | 35% | 60% |
| 1 hour 40 minutes | 28% | 19% |
| 4 hours 30 minutes | 28% | 14% |

These results show the protection against hydrolysis of the bidentate ligands or second ligand, thus permitting economizing the more expensive ligand by reducing the rate of hydrolysis as well as the quantity of bidentate ligand with respect to the metallic element, while conserving the level of catalytic activity of the system including the second ligand.

Each patent, patent application and literature article/report cited or indicated herein is hereby expressly incorporated by reference.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. Process of hydrocyanation of compounds, wherein said compounds having at least one site of ethylenic unsaturation selected from the group consisting of diolefins and ethylenically unsaturated nitriles which comprises reacting said compounds with hydrogen cyanide in the presence of a catalyst having the general formula (III):

M[L$_1$]$_x$[L$_2$]$_y$ (III)

wherein M is a catalytically active transition metal; L$_1$ is a monodentate organophosphorus first ligand; L$_2$ is a pluridentate organophosphorus second ligand; and x and y are each a decimal number corresponding to the number of moles of the respective ligand in the catalytic system.

2. Process according to claim 1, wherein the second organophosphorus ligand is a bidentate ligand.

3. Process according to claim 1, wherein the second ligand is selected from the group consisting of organophosphite, organophosphine, organophosphinite, organophosphonite, and organophosphoramide compounds.

4. Process according to claim 1, wherein the ratio of the number of second pluridentate ligands expressed in atoms of phosphorus to the number of atoms of metallic element is greater than 0.5.

5. Process according to claim 1, wherein the ratio of the total number of moles of first and second ligands, expressed as the number of phosphorus atoms, to the number of atoms of metallic element, is comprised between 1 and 100.

6. Process according to claim 1, wherein the ratio of the total number of moles of first ligand to the number of moles of second ligand is greater than 0.1.

7. Process according to claim 1, wherein the first, monodentate ligand has the following general formula (I):

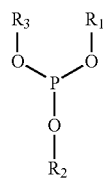

(I)

wherein R$_1$, R$_2$, and R$_3$, which may be identical or different, are each a linear or branched alkyl radical having 1–12 carbon atoms and optionally containing one or two oxygen atoms; an aromatic or cycloaliphatic radical, substituted or unsubstituted, also optionally containing one or two oxygen atoms; and one or two ring members, whether or not in condensed form, with the proviso that the radicals R$_1$, R$_2$, R$_3$ may be bonded together.

8. Process according to claim 7, wherein the second ligand has the general formula (II):

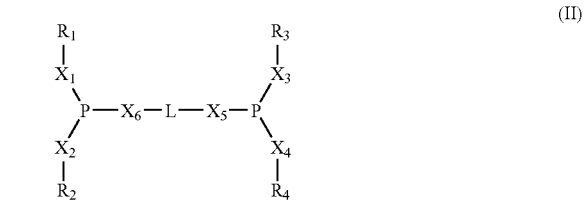

(II)

wherein R$_1$, R$_2$, R$_3$, and R$_4$, which may be identical or different, are each a linear or branched alkyl radical having 1–12 carbon atoms, optionally containing one or two oxygen atoms; an aromatic or cycloaliphatic radical, substituted or unsubstituted, also optionally containing one or two oxygen atoms and one or more ring members, whether or not in condensed form; an alkylaryl radical; or an arylalkyl radical; with the proviso that the radicals R$_1$ and R$_2$, and/or R$_3$ and R$_4$, can be bonded together; X$_1$, X$_2$, X$_3$, X$_4$, X$_5$, and X$_6$, which may be identical or different, are each a covalent bond, an oxygen atom, or a divalent NR$_5$ radical in which R$_5$ is a hydrogen atom or an alkyl, aryl, sulfonyl, cycloalkyl, or carbonylated radical, and L is a covalent bond or a divalent, linear alkyl radical having 1–12 carbon atoms, optionally containing one or two oxygen atoms; a divalent cycloaliphatic or aromatic radical, also optionally containing one or two oxygen atoms, substituted or unsubstituted, optionally including at least one ring member, whether or not in condensed form; or a divalent alkylaryl or arylalkyl radical.

9. Process according to claim 1, wherein the monodentate first ligand is selected from the group consisting of triphenyl phosphite, tritolyl phosphite, trithymol phosphite, and the bidentate second ligand is selected from the group consisting of the compounds of the following formulas:

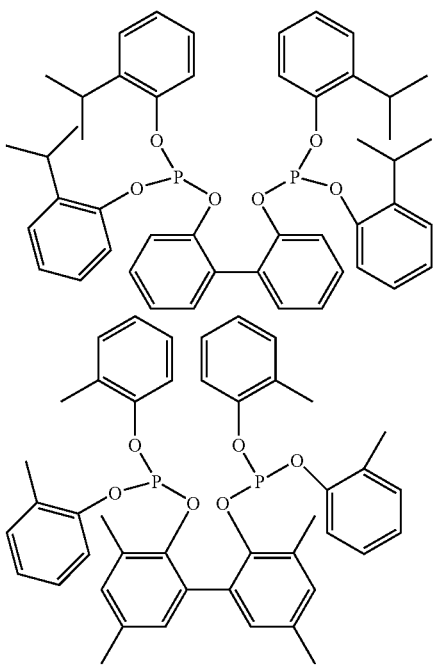

-continued

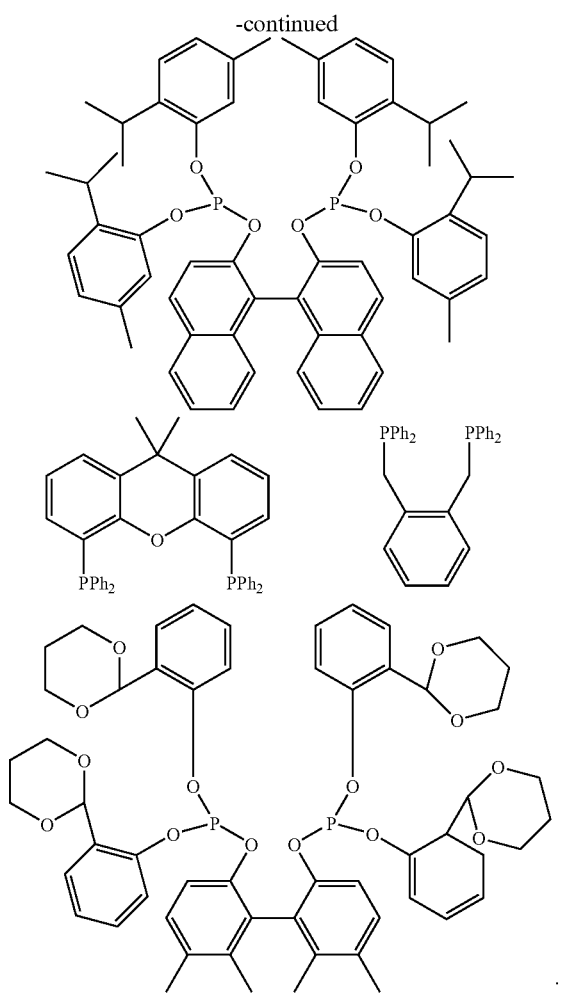

10. Process according to claim 1, wherein the reaction is performed in a single-phase medium.

11. Process according to claim 1, wherein the transition metal is selected from the group consisting of nickel, cobalt, iron, ruthenium, rhodium, palladium, osmium, iridium, platinum, copper, silver, gold, zinc, cadmium, and mercury.

12. Process according to claim 1, wherein the reaction medium includes a solvent for the catalyst, miscible with the phase comprising the compound to undergo hydrocyanation at the temperature of hydrocyanation.

13. Process according to claim 1, wherein the transition metal is nickel and the catalyst is selected from the group consisting of compounds in which the nickel has a degree of oxidation as zero, potassium tetracyanonickelate $K_4[Ni(CN)_4]$, bis(acrylonitrile) nickel zero, bis(1,5-cyclooctadiene) nickel, derivatives containing ligands, tetrakis (triphenylphosphine) nickel zero; nickel compounds, nickel carboxylates, carbonate, bicarbonate, borate, bromide, chloride, citrate, thiocyanate, cyanide, formate, hydroxide, hydrophosphite, phosphite, phosphate and derivatives, iodide, nitrate, sulfate, sulfite, aryl and alkyl sulfonates.

14. Process according to claim 1, wherein the compounds having at least one site of ethylenic unsaturation are selected from the group consisting of diolefins, butadiene, isoprene, 1,5-hexadiene, 1,5-cyclooctadiene, aliphatic nitriles having ethylenic unsaturation, linear pentenenitriles, pentene-3-nitrile, pentene-4-nitrile, and mixtures thereof.

15. Process according to claim 8, wherein the quantity of nickel or other transition metal compound employed is selected such that there are between $10^{-4}$ and 1 mole of nickel or other transition metal used per mole of organic compound to undergo hydrocyanation or isomerization, and the quantity of compound of formula (I) or formula (II) used is chosen such that the number of moles of this compound with respect to 1 mole of transition metal is 0.5–100.

16. Process according to claim 1, wherein the hydrocyanation reaction is performed at temperature of 10° C. to 200° C.

17. Process of hydrocyanation to dinitriles of ethylenically unsaturated nitriles, by reaction with hydrogen cyanide, performed in the presence of a catalyst according to claim 1 and a co-catalyst comprising at least one Lewis acid.

18. Process according to claim 17, wherein the ethylenically unsaturated nitriles are selected from the group consisting of ethylenically unsaturated aliphatic nitriles, linear pentenenitriles, pentene-3-nitrile, pentene-4-nitrile, and mixtures thereof.

19. Process according to claim 18, wherein the linear pentenenitriles contain quantities of other compounds selected from the group consisting of 2-methyl-3-butenenitrile, 2-methyl-2-butenenitrile, 2-pentenenitrile, valeronitrile, adiponitrile, 2-methyl glutaronitrile, 2-ethyl succinonitrile, or butadiene.

20. Process according to claim 17, wherein the Lewis acid co-catalyst is selected from the group consisting of compounds of elements of Groups Ib, IIb, IIIa, IIIb, IVa, IVb, Va, Vb, VIb, VIIb and VIII of the Periodic Table of the elements.

21. Process according to claim 17, wherein the Lewis acid is selected from the group consisting of halides, sulfates, halogenoalkyl sulfonates, perhalogenoalkyl sulfonates, halogenoacetates, perhalogenoacetates, carboxylates, and phosphates.

22. Process according to claim 17, wherein the Lewis acid is selected from the group consisting of zinc chloride, zinc bromide, zinc iodide, manganese chloride, manganese bromide, cadmium chloride, cadmium bromide, stannous chloride, stannous bromide, stannous sulfate, stannous tartrate, indium chloride, indium trifluoromethylsulfonate, indium trifluoroacetate, the chlorides or bromides of the rare earth elements lanthanum, cerium, praseodymium, neodymium, samarium, europium, gadolinium, terbium, dysprosium, hafnium, erbium, thallium, ytterbium and lutetium, cobalt chloride, ferrous chloride, and yttrium chloride, triphenylborane and titanium isopropylate, and mixtures thereof.

23. Process according to claim 17, wherein the Lewis acid used represents 0.01–50 moles per mole of transition metal compound.

* * * * *